④ United States Patent [19]
Yamada et al.
[11] Patent Number: 4,507,284
[45] Date of Patent: * Mar. 26, 1985

[54] SOIL DISINFECTANT

[75] Inventors: Yoshimi Yamada, Hyogo; Tadashi Ooishi, Osaka; Toshiro Kato; Kunio Mukai, both of Hyogo, all of Japan

[73] Assignee: Sumitomo Chemical Company, Limited, Osaka, Japan

[ * ] Notice: The portion of the term of this patent subsequent to Dec. 28, 1999 has been disclaimed.

[21] Appl. No.: 413,141

[22] Filed: Aug. 30, 1982

Related U.S. Application Data

[62] Division of Ser. No. 210,618, Nov. 26, 1980, Pat. No. 4,366,150.

[30] Foreign Application Priority Data

Nov. 29, 1979 [JP] Japan ................................ 54-155061
Apr. 30, 1980 [JP] Japan ................................ 55-58477

[51] Int. Cl.$^3$ ............................................ A01N 57/00
[52] U.S. Cl. ............................................ 514/140; 424/199; 424/222
[58] Field of Search ........................ 424/222, 198, 199

[56] References Cited

U.S. PATENT DOCUMENTS

| | | | |
|---|---|---|---|
| 3,280,131 | 10/1966 | Wakeman et al. | 424/199 |
| 4,366,150 | 12/1982 | Yamada et al. | 424/199 |

OTHER PUBLICATIONS

*Chemical Abstracts*, vol. 50, No. 11, Jun. 10, 1956, 8122h.
Beilsteins Handbuch der Organischen Chemie, 4th Edition, vol. 1, (Berlin 1933), p. 791, lines 1-33.
Reaves, *Chem. Abstracts*, vol. 70, (1969), No. 107, 463a.
Wakeman et al., *Chem. Abstracts*, vol. 66, (1967) No. 2637y.
Chemical Abstracts, vol. 50, (1956), 8122h, 11595h; P. Craniadès "New Cytoactive Products in a Series of Phosphonic Acid Derivatives".
Chemical Abstracts, vol. 70, (1969); 107463A; A. Reaves, "Polymerization in the Presence of a Phosphinate".

*Primary Examiner*—Leonard Schenkman
*Assistant Examiner*—Joseph A. Lipovsky
*Attorney, Agent, or Firm*—Birch, Stewart, Kolasch & Birch

[57] ABSTRACT

A soil disinfectant composition for preventing and controlling diseases caused by pathogenic fungi living in soil, which comprises an effective amount of at least one of phenylphosphinic acid and its salts as an active ingredient, and at least one inert carrier or diluent.

11 Claims, No Drawings

SOIL DISINFECTANT

This application is a divisional of copending application Ser. No. 210,618, filed on Nov. 26, 1980 now U.S. Pat. No. 4,366,150.

The present invention relates to a soil disinfectant. More particularly, it relates to a soil disinfectant which is highly effective in preventing and controlling pathogenic fungi living in soil with promotion of the growth of crop plants and without exertion of any material toxicity to mammals and fish.

Soil-infectious diseases of crop plants are caused by the infection of plant pathogens living in soil and are difficult to prevent and control. Although several kinds of soil disinfectants are already in the practical use, their preventing and controlling effect is still unsatisfactory.

On the other hand, environmental pollution by agricultural chemicals has become serious in recent years, and there is a great demand for developing agricultural chemicals which are low in toxicity to mammals and fish and decompose rapidly so as to remain in crop plants for a long period of time.

As the result of an extensive study, it has now been found that phenylphosphinic acid and its salts exhibit an excellent effect in preventing and controlling diseases caused by phyto-pathogens living in soil, particularly diseases caused by *Fusarium oxysporum,* for example, yellows of Japanese radish (*Fusarium oxysporum* f. sp. *raphani*), fusarium wilt of tomato (*Fusarium oxysporum* f. sp. *lycopersici*), fusarium wilt of cucumber (*Fusarium oxysporum* f. sp. *cucumerinum*), yellows of cabbage (*Fusarium oxysporum* f. sp. *conglutinans*), yellows of strawberry (*Fusarium oxysporum* f. sp. *fragariae*), fusarium wilt of melon (*Fusarium oxysporum* f. sp. *melonis*) and fusarium wilt of watermelon (*Fusarium oxysporum* f. sp. *niveum*). It has also been found that they have an action to promote the growth of roots and leaves of crop plants with activation of their entire body. Advantageously, they do not cause any chemical injury to crop plants and are scarcely retained in crop plants over a long period of time. In addition, they are materially non-toxic to warm-blooded animals (e.g. mice, rats, dogs, chickens) and fish (e.g. carp, gold fishes, cyprinodonts). Thus, phenylphosphinic acid and its salts can be said to be ideal soil-disinfectants.

According to the present invention, there is provided a soil-disinfectant which comprises as an active ingredient at least one of phenylphosphinic acid and its salts.

Phenylphosphinic acid to be used as an active ingredient in this invention is a well-known compound, which is easily available from the market. Also, it can be readily synthesized by the well-known method (Beil. 16, 791).

The salts of phenylphosphinic acid may be the ones with organic or inorganic bases, which may be produced, for instance, by treating phenylphosphinic acid with an organic or inorganic base at a temperature from room temperature to about 100° C. for a period of about 10 minutes to about 1 hour, usually in an inert solvent such as alcohols (e.g. methanol, ethanol), chloroform, tetrahydrofuran, acetonitrile or water. Examples of the inorganic base include lithium hydroxide, sodium hydroxide, potassium hydroxide, ammonia, hydrazine, etc. Examples of the organic base are amines such as aliphatic amines, particularly alkylamines (e.g. methylamine, ethylamine, n-propylamine, isopropylamine, n-butylamine, isobutylamine, sec-butylamine, t-butylamine, n-amylamine, isoamylamine, n-hexylamine, 2-methylpentylamine, cyclopentylamine, cyclohexylamine), alkenylamines (e.g. allylamine), dialkylamines (e.g. dimethylamine, diethylamine, methylethylamine, di-n-propylamine, diisopropylamine, di-n-butylamine, diisobutylamine), dialkenylamines (e.g. diallylamine), trialkylamines (e.g. trimethylamine, triethylamine, tri-n-propylamine, tri-n-butylamine, dimethylcyclohexylamine) and alkylenediamines (e.g. ethylenediamine, trimethylenediamine, N,N-dimethylethylenediamine, N,N'-dimethyltrimethylenediamine, N,N,N',N'-tetramethylethylenediamine, N,N-dimethyltrimethylenediamine, N,N,N',N'-tetramethyltrimethylenediamine, 1,2-diaminocyclohexane, N,N-dimethyl-1,2-diaminocyclohexane), aralkylamines (e.g. benzylamine, α-phenethylamine, β-phenethylamine, methylbenzylamine, methylphenethylamine, α,α-dimethylbenzylamine, 2-(2-thienyl)ethylamine, 2-(2-furyl)ethylamine, furfurylamine, 2-thienylmethylamine) and alcoholamines (e.g. ethanolamine, N-methylethanolamine, N-isopropylethanolamine, N,N-dimethylethanolamine, diethanolamine, triethanolamine, tris(hydroxymethyl)aminomethane, diglycolamine), aromatic amines, particularly anilines (e.g. aniline, N-methylaniline, diphenylamine, 4-fluoroaniline, 4-chloroaniline, 4-bromoaniline, 4-iodoaniline, 2,4-dichloroaniline, 2,5-dichloroaniline, 3,5-dichloroaniline, 2,4,6-trichloroaniline, 3-trifluoromethylaniline, 4-nitroaniline, 2-methyl-4-methoxyaniline, 3-fluoroaniline, 3-chloroaniline, 3-bromoaniline, 3-iodoaniline, 2,6-dimethylaniline, 2,6-diethylaniline, 4-methylaniline, 3-tert-butylaniline), and cyclic amines (e.g. pyrrolidine, piperidine, morpholine, 2-methylpiperidine, 2,6-dimethylmorpholine, piperazine, 4-methylpiperazine, triethylenediamine) and heteroaromatic compounds containing at least one N-atom as the constituent of the ring (e.g. pyridine, α-picoline, β-picoline, γ-picoline, 2,6-lutidine, collidine, 2-amino-3-methylpyridine, 2,2'-bipyridyl, 4,4'-bipyridyl, 2,4'-bipyridyl, pyrazole, triazole, imidazole, triazine, pyrazine, pyrimidine, thiazole, oxazole, isoxazole, quinoline, isoquinoline, pyrrole); N-substituted hydrazines (e.g. N-methylhydrazine, N,N-dimethylhydrazine, N-phenylhydrazine, N-3-acetylphenylhydrazine); imines (e.g. N-benzylidene-tert-butylamine, N,N'-bis(-sec-butyl)-p-xylylenediimine, N,N'-bis(4-chlorobenzylidene)ethylenediamine, N-benzylideneaniline, N-isopropylideneethanolamine, N,N'-bis(4-chlorophenyl)-p-xylylenediimine), etc.

The salts of phenylphosphinic acid may be also the metal salts (except alkaline metal salts), which may be prepared, for instance, by treatment of an alkaline metal salt of phenylphosphinic acid with a carbonate, acetate, nitrate or halide of a metal other than an alkaline metal, at a temperature of from room temperature to about 100° C. for a period of several minutes to about 1 hour, usually in an inert solvent (e.g. water, aqueous methanol, aqueous ethanol). If necessary, the product may be purified, for example, by recrystallization.

Still, the said alkaline metal salt of phenylphosphinic acid can easily be synthesized from phenylphosphinic acid and an alkaline metal hydroxide, usually in the presence of an inert solvent (e.g. water, aqueous methanol, aqueous ethanol). The reaction mixture thus obtained may be as such used without isolation of the alkaline metal salt of phenylphosphinic acid therefrom.

Examples of the metallic salts usable for the reaction with the alkaline metal salt of phenylphosphinic acid are as follows: carbonates such as calcium(II) carbonate, barium(II) carbonate and thallium(I) carbonate; acetates such as zinc(II) acetate, calcium(II) acetate, barium(II) acetate, magnesium(II) acetate, manganese(II) acetate, nickel(II) acetate, cobalt(II) acetate and copper(II) acetate; nitrates such as calcium(II) nitrate, barium(II) nitrate, magnesium(II) nitrate, aluminum(III) nitrate, manganese(II) nitrate, iron(III) nitrate, zinc(II) nitrate, nickel(II) nitrate, copper(II) nitrate and cobalt(II) nitrate; chlorides such as calcium(II) chloride, barium(II) chloride, magnesium(II) chloride, iron(II) chloride, iron(III) chloride, zinc(II) chloride, tin(II) chloride, tin(IV) chloride, nickel(II) chloride, copper(II) chloride, cobalt(II) chloride and titanium(IV) chloride, etc.

Specific examples of phenylphosphinic acid and its salts usable as the active ingredient in this invention are shown in Table 1.

TABLE 1

| Compound No. | Chemical structure | Physical property |
|---|---|---|
| 1 | 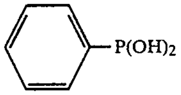 | M.P., 83-85° C. |
| 2 | 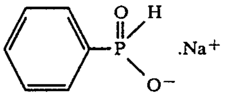 | M.P., >260° C. |
| 3 | 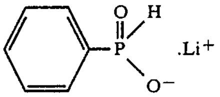 | M.P., >280° C. |
| 4 | 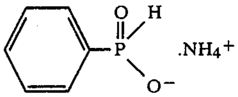 | M.P., 137-142° C. |
| 5 | 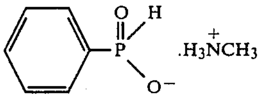 | $n_D^{19.6}$ 1.5293 |
| 6 | 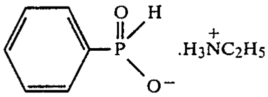 | $n_D^{19.6}$ 1.5256 |
| 7 | 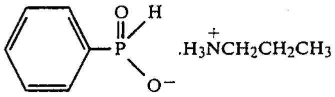 | $n_D^{19.6}$ 1.5058 |
| 8 | 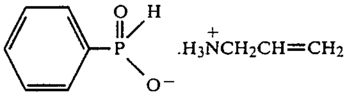 | $n_D^{19.6}$ 1.4530 |
| 9 | 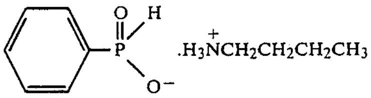 | M.P., 62-66° C. |
| 10 | 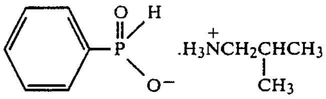 | M.P., 79-81° C. |
| 11 | 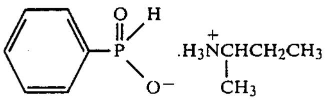 | M.P., 87-89° C. |

TABLE 1-continued
| Compound No. | Chemical structure | Physical property |
|---|---|---|
| 12 | 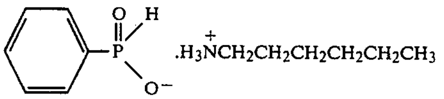 | M.P., 72–75° C. |
| 13 | 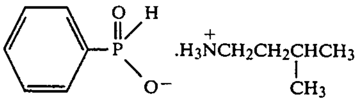 | M.P., 89–93° C. |
| 14 | 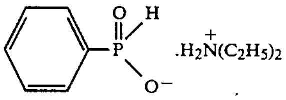 | $n_D^{28.2}$ 1.5038 |
| 15 | 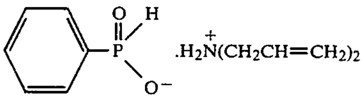 | $n_D^{27.3}$ 1.5128 |
| 16 | 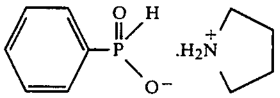 | $n_D^{24.3}$ 1.5286 |
| 17 | 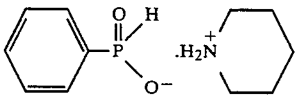 | $n_D^{24.3}$ 1.5303 |
| 18 | 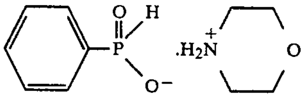 | M.P., 66–71° C. |
| 19 | 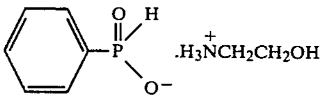 | $n_D^{25.2}$ 1.5228 |
| 20 | 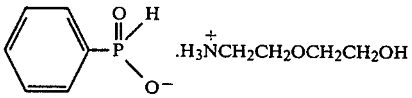 | $n_D^{26.2}$ 1.5134 |
| 21 | 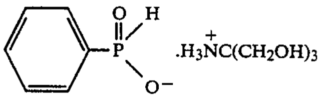 | M.P., 127–130° C. |
| 22 | 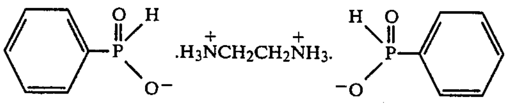 | M.P., 157–161° C. |
| 23 | 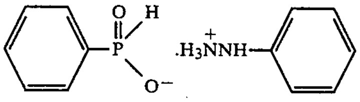 | M.P., 136–140° C. |
| 24 | 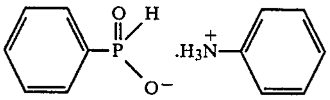 | M.P., 97–102° C. |

TABLE 1-continued
| Compound No. | Chemical structure | Physical property |
| --- | --- | --- |
| 25 | 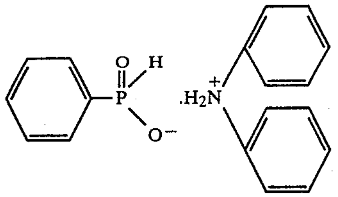 | M.P., 40–42° C. |
| 26 | 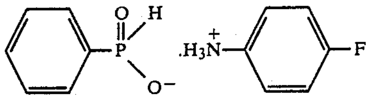 | M.P., 113–117° C. |
| 27 | 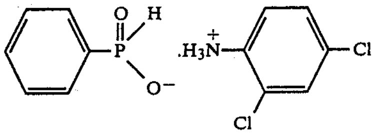 | M.P., 46–49° C. |
| 28 | 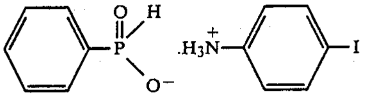 | M.P., 108–112° C. |
| 29 | 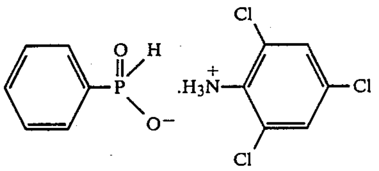 | M.P., 57–59° C. |
| 30 | 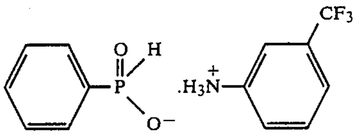 | M.P., 72–76° C. |
| 31 | 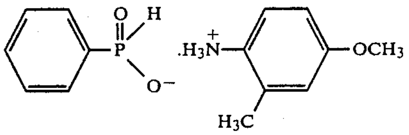 | M.P., 86–89° C. |
| 32 | 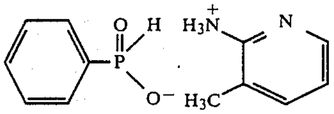 | M.P., 115–117° C. |
| 33 | 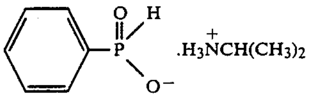 | M.P., 50–55° C. |
| 34 | 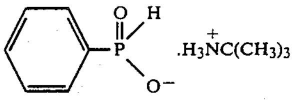 | M.P., 155–160° C. |
| 35 | 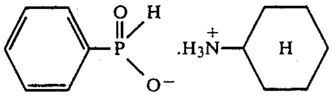 | M.P., 190–195° C. |

TABLE 1-continued
| Compound No. | Chemical structure | Physical property |
|---|---|---|
| 36 | 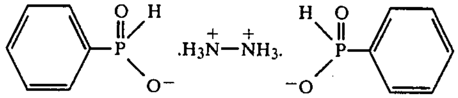 | M.P., 93-97° C. |
| 37 | 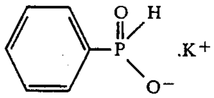 | M.P., >280° C. |
| 38 | 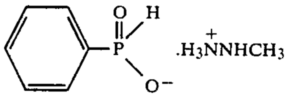 | $n_D^{21.4}$ 1.5300 |
| 39 | 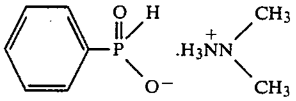 | $n_D^{21.4}$ 1.5278 |
| 40 | 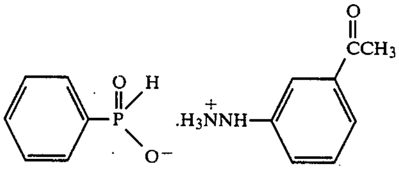 | M.P., 64-68° C. |
| 41 | 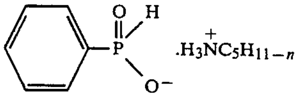 | M.P., 60-65° C. |
| 42 | 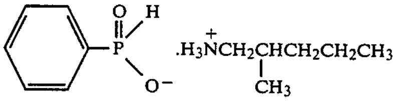 | M.P., 65-72° C. |
| 43 | 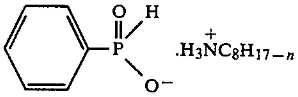 | M.P., 67-72° C. |
| 44 | 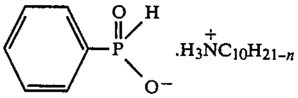 | M.P., 54-57° C. |
| 45 | 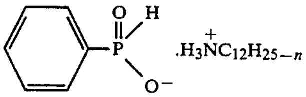 | M.P., 46-51° C. |
| 46 | 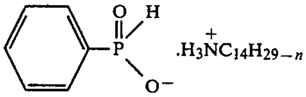 | M.P., 56-61° C. |
| 47 | 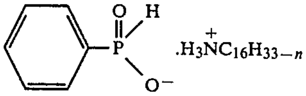 | M.P., 60-65° C. |

TABLE 1-continued
| Compound No. | Chemical structure | Physical property |
| --- | --- | --- |
| 48 | 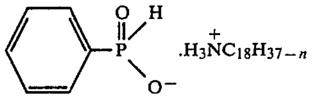 | M.P., 70–75° C. |
| 49 | 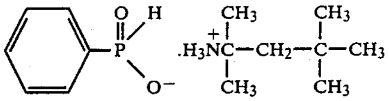 | M.P., 170–175° C. |
| 50 | 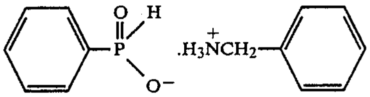 | M.P., 65–70° C. |
| 51 | 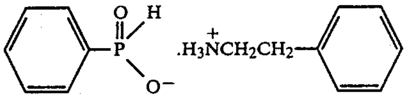 | M.P., 123–126° C. |
| 52 | 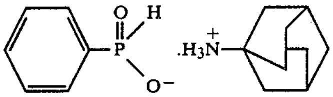 | M.P., 250–260° C. |
| 53 | 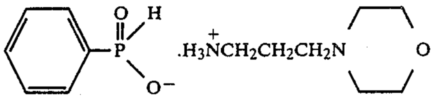 | M.P., 95–99° C. |
| 54 | 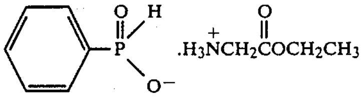 | M.P., 110–115° C. |
| 55 | 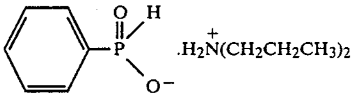 | $n_D^{27.4}$ 1.4928 |
| 56 | 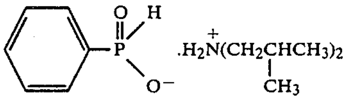 | M.P., 85–90° C. |
| 57 | 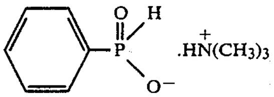 | $n_D^{22.0}$ 1.4862 |
| 58 | 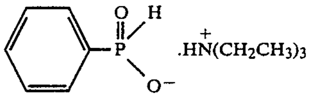 | $n_D^{25.6}$ 1.5110 |
| 59 | 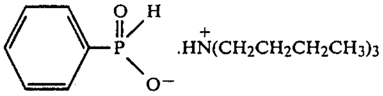 | M.P., 35–39° C. |
| 60 | 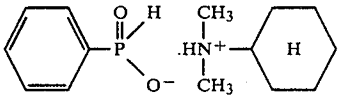 | $n_D^{26.2}$ 1.5120 |

TABLE 1-continued
| Compound No. | Chemical structure | Physical property |
|---|---|---|
| 61 | 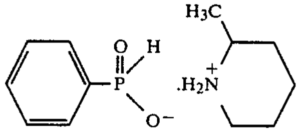 | $n_D^{20.0}$ 1.5237 |
| 62 | 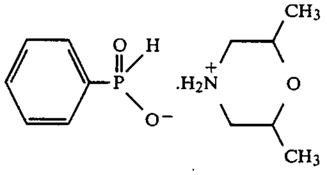 | $n_D^{21.5}$ 1.5155 |
| 63 | 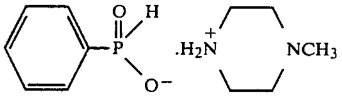 | M.P., 55-60° C. |
| 64 | 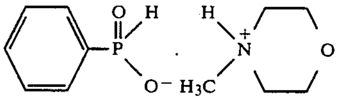 | $n_D^{21.5}$ 1.5465 |
| 65 | 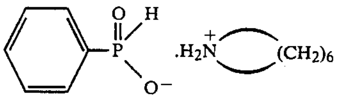 | $n_D^{21.5}$ 1.5404 |
| 66 | 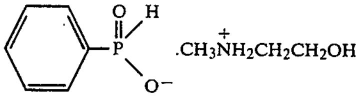 | $n_D^{25.2}$ 1.5298 |
| 67 | 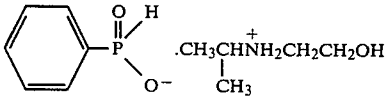 | $n_D^{25.2}$ 1.5083 |
| 68 | 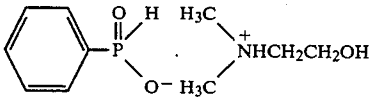 | $n_D^{25.2}$ 1.5163 |
| 69 | 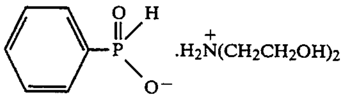 | $n_D^{25.2}$ 1.5058 |
| 70 | 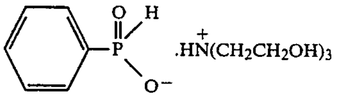 | $n_D^{25.2}$ 1.5300 |
| 71 | 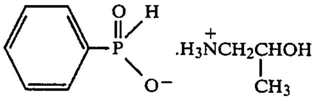 | $n_D^{21.5}$ 1.5358 |
| 72 | 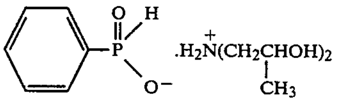 | $n_D^{21.5}$ 1.5256 |

TABLE 1-continued
| Compound No. | Chemical structure | Physical property |
|---|---|---|
| 73 | 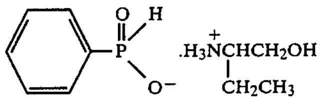 | M.P., 102–105° C. |
| 74 | 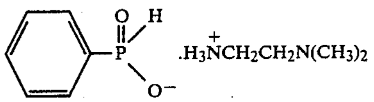 | $n_D^{26.5}$ 1.5220 |
| 75 | 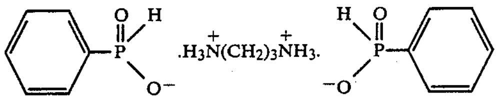 | M.P., 230–235° C. |
| 76 | 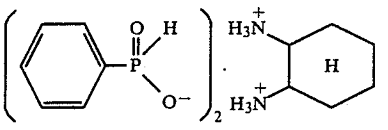 | M.P., 240–245° C. |
| 77 | 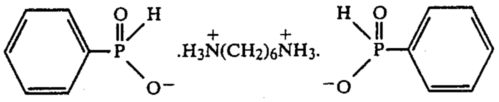 | M.P., 132–135° C. |
| 78 | 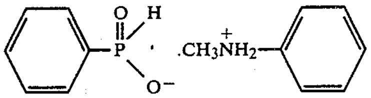 | $n_D^{27.7}$ 1.5594 |
| 79 | 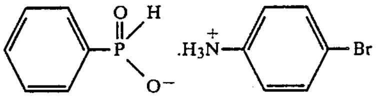 | M.P., 112–117° C. |
| 80 | 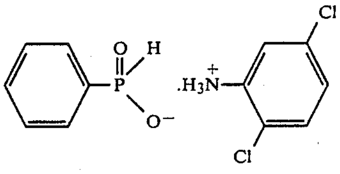 | $n_D^{27.1}$ 1.5800 |
| 81 | 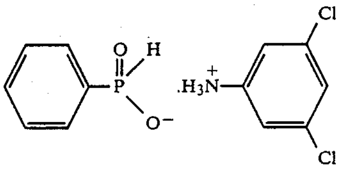 | $n_D^{21.3}$ 1.5837 |
| 82 | 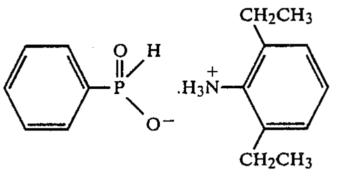 | M.P., 44–46° C. |
| 83 | 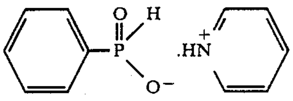 | $n_D^{25.0}$ 1.5572 |

TABLE 1-continued
| Compound No. | Chemical structure | Physical property |
|---|---|---|
| 84 | 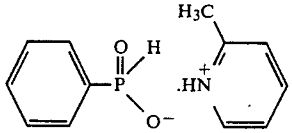 | $n_D^{24.8}$ 1.5544 |
| 85 | 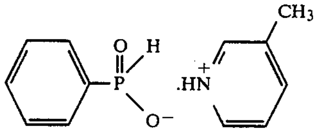 | $n_D^{24.8}$ 1.5608 |
| 86 | 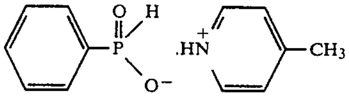 | $n_D^{25.0}$ 1.5442 |
| 87 | 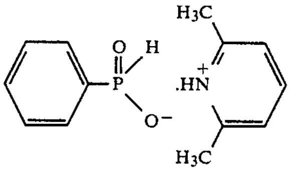 | $n_D^{25.0}$ 1.5572 |
| 88 | 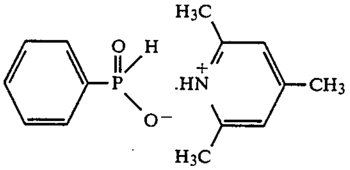 | $n_D^{25.0}$ 1.5460 |
| 89 | 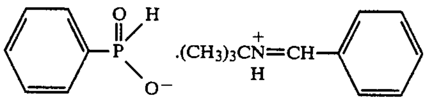 | M.P., 205-210° C. |
| 90 | 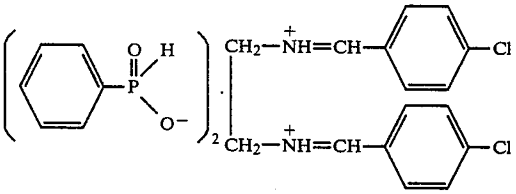 | $n_D^{25.0}$ 1.5705 |
| 91 | 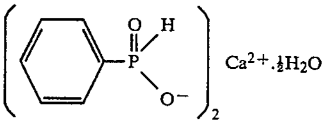 | M.P., >280° C. |
| 92 | 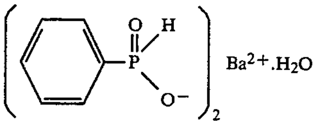 | M.P., >280° C. |
| 93 | 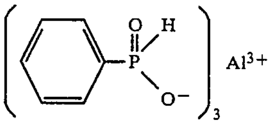 | M.P., >260° C. |

TABLE 1-continued
| Compound No. | Chemical structure | Physical property |
|---|---|---|
| 94 | 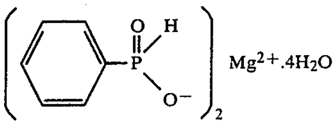 | M.P., 205–210° C. |
| 95 | 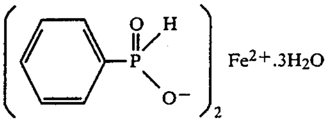 | M.P., >260° C. |
| 96 | 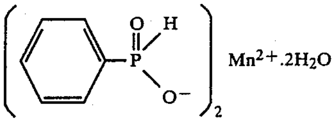 | M.P., >260° C. |
| 97 | 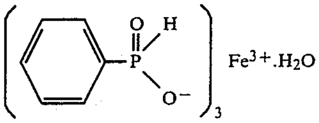 | M.P., >270° C. |
| 98 | 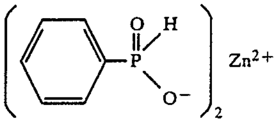 | M.P., 238–241° C. |
| 99 | 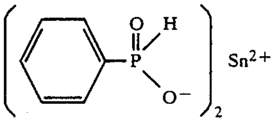 | M.P., 165–168° C. |
| 100 | 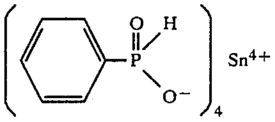 | M.P., >280° C. |
| 101 | 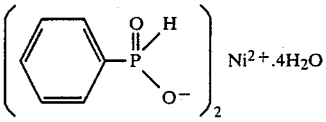 | M.P., >280° C. |
| 102 | 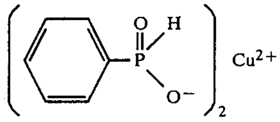 | M.P., 128–132° C. |
| 103 | 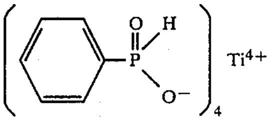 | M.P., >280° C. |

TABLE 1-continued

| Compound No. | Chemical structure | Physical property |
|---|---|---|
| 104 | 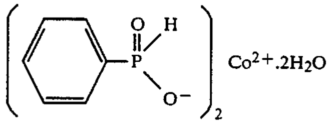 | M.P., 218-223° C. |

When phenylphosphinic acid or its salt is applied together or in combination with any other disinfectant or fungicide, its preventing and controlling effect on soil-infectious diseases is significantly increased. Examples of such disinfectants or fungicides are N-trichloromethylthiotetrahydrophthalimide, pentachloronitrobenzene, 5-ethoxy-3-trichloromethyl-1,2,4-thiadiazole, 5-methyl-3-hydroxy-1,2-oxazole, 1,4-dichloro-2,5-dimethoxybenzene, O,O-dimethyl O-(2,6-dichloro-4-methylphenyl)phosphorothioate, DL-methyl-N-(2,6-dimethylphenyl)-N-(2-methoxyacetyl)alanylate, DL-methyl-N-(2,6-dimethylphenyl)-N-(2-furyl-)alanylate, N-(3,5-dichlorophenyl)-1,2-dimethylcyclopropane-1,2-dicarboximide, 1,2-bis(3-methoxycarbonyl-2-thioureido)benzene, methyl-1-(butylcarbamoyl)benzimidazol-2-ylcarbamate, etc. If desired, other effective materials such as disinfectants, fungicides, nematocides, insecticides, herbicides and fertilizers may be also employed together with phenylphosphinic acid or its salt.

For the practical use, phenylphosphinic acid or its salt may be applied as such or in any conventional preparation form such as dusts, granules, fine granules, wettable powders, emulsifiable concentrates or liquids. It is desirable that these preparations are properly used depending on the purpose as intended. Also, they may be applied by various means such as spraying, dusting, scattering, soil treatment, seed-dressing, dipping and fumigation.

Generally, the preparations may contain phenylphosphinic acid or its salt in an amount of 1.0 to 80% by weight, preferably 2.0 to 60.0% by weight, on the basis of the total weight of the components and applied at a rate of 1 to 10 kg per 10 ares. The concentration of the active ingredient on the application is preferably within a range of 0.01 to 1.0%. Since, however, the amount and concentration are associated with various factors such as preparation forms, application time, technique and place of application, diseases to be controlled and crop plants to be protected, they may properly be decided irrespective of the foregoing ranges.

For formulation of the preparations, there may be employed conventional solid or liquid carriers or diluents. Examples of solid carriers or diluents include talc, bentonite, clay, kaolin, diatomaceous earth, vermiculite, etc. Liquid carriers or diluents include, for example, water, benzene, alcohols, acetone, xylene, dioxane, methylnaphthalene, cyclohexanone, etc. There may be also employed conventional emulsifiers such as alkyl sulfates, alkylsulfonates, arylsulfonates, polyethylene glycol ethers and polyhydric alcohol esters.

This invention will be illustrated in more detail with reference to the following examples, wherein part(s) and % are by weight unless otherwise indicated.

REFERENCE EXAMPLE 1

(Preparation of Compound No. 4)

To a heterogeneous mixture of phenylphosphinic acid (17.86 g; 0.1257 mole) and methanol (15 ml) was added dropwise 29.3% aqueous ammonia (7.30 g; 0.1258 mole) with stirring and cooling. The resulting homogeneous solution was stirred for 30 minutes at room temperature, and the solvent was then removed under reduced pressure while maintaining the bath temperature below 40°-50° C. Thereafter, azeotropic drying was carried out twice each with methanol and then with benzene, and the white powder obtained was vacuum dried over silica gel at room temperature. Yield, 19.66 g (98.3%). M.P., 137°-142° C. (softened at 125°-130° C.). (The melting point was measured with a melting point microtester MP-P manufactured by Mitamura Riken Kogyo Co., Ltd.; not corrected).

Elementary analysis: Calcd. for $C_6H_{10}NO_2P$: C, 45.29%; H, 6.33%; N, 8.80%; P, 19.46%. Found: C, 45.15%; H, 6.56%; N, 8.74%; P, 19.38%.

In the same manner as above, Compound Nos. 2, 3 and 5 to 90 were prepared.

REFERENCE EXAMPLE 2

(Preparation of Compound No. 98)

Phenylphosphinic acid (2.84 g; 0.02 mole) was added, with stirring, to a solution of sodium hydroxide (0.80 g; 0.02 mole) in water (5.0 g) to make an aqueous solution of sodium phenylphosphinate.

To this aqueous solution was added dropwise a solution of zinc acetate dihydrate (2.85 g; 0.013 mole) in water (5.0 g) with stirring. After stirring at room temperature for 30 minutes, the precipitated white solid was collected by filtration, washed with two 2-ml portions of water and vacuum dried. Yield, 3.28 g (94.4%). M.P., 238°-241° C.

Elementaly analysis: Calcd. for $C_{12}H_{12}O_4P_2Zn$: C, 41.47%; H, 3.48%; P, 17.82%. Found: C, 41.35%; H, 3.33%; P, 17.54%.

In the same manner as above, Compound Nos. 91 to 97 and 99 to 104 were prepared.

PREPARATION EXAMPLE 1

(Dust)

Two parts of Compound No. 1 and 98 parts of clay were well mixed while being powdered to obtain a dust containing 2% of the active ingredient. On application, it was scattered as such or well mixed with soil.

PREPARATION EXAMPLE 2

(Wettable powder)

Fifty parts of Compound No. 4, 5 parts of a wetting agent (alkylbenzenesulfonate type) and 45 parts of diatomaceous earth were well mixed while being powdered to obtain a wettable powder containing 50% of the active ingredient. On application, it was diluted with water and then sprayed or perfused to soil.

PREPARATION EXAMPLE 3

(Emulsifiable concentrate)

Twenty parts of Compound No. 18, 20 parts of cyclohexanone, 40 parts of xylene and 20 parts of an emulsifier (polyoxyethylene phenylphenol polymer type) were well mixed to obtain an emulsifiable concentrate containing 20% of the active ingredient. On application, it was diluted with water and then sprayed or perfused to soil.

PREPARATION EXAMPLE 4

(Granule)

Ten parts of Compound No. 42, 85 parts of silica powder, 4.95 parts of calcium lignosulfonate and 0.05 part of sodium alkylbenzenesulfonate were well mixed while being powdered. The powder obtained was kneaded with water, granulated and dried to obtain a granule containing 10% of the active ingredient. On application, it was scattered on soil as such or well mixed with soil.

PREPARATION EXAMPLE 5

(Liquid)

Sixty parts of Compound No. 2 and 5 parts of a wetting agent (alkylbenzenesulfonate type) were dissolved in 35 parts of water to obtain a liquid containing 60% of the active ingredient. On application, it was diluted with water and then sprayed or perfused to soil.

PREPARATION EXAMPLE 6

(Composite dust)

Five parts of Compound No. 4, 5 parts of pentachloronitrobenzene and 90 parts of clay were well mixed while being powdered to obtain a composite dust containing 10% of the active ingredients.

PREPARATION EXAMPLE 7

(Composite liquid)

Twenty-five parts of Compound No. 18, 25 parts of 5-methyl-3-hydroxy-1,2-oxazole and 5 parts of a wetting agent (alkylbenzenesulfonate type) were dissolved in 45 parts of water to obtain a composite liquid containing 50% of the active ingredients.

PREPARATION EXAMPLE 8

(Composite granule)

Six parts of Compound No. 19, 4 parts of 1,4-dichloro-2,5-dimethoxybenzene, 85 parts of silica powder, 4.95 parts of calcium lignosulfonate and 0.05 part of sodium alkylbenzenesulfonate were well mixed while being powdered. The powder obtained was then kneaded with water, granulated and dried to obtain a composite granule containing 10% of the active ingredients.

PREPARATION EXAMPLE 9

(Dust)

Ten parts of Compound No. 91 and 90 parts of clay were well mixed while being powdered to obtain a dust containing 10% of the active ingredient. On application, it was scattered as such or well mixed with soil.

PREPARATION EXAMPLE 10

(Wettable powder)

Fifty parts of Compound No. 93, 5 parts of a wetting agent (alkylbenzenesulfonate type) and 45 parts of diatomaceous earth were well mixed while being powdered to obtain a wettable powder containing 50% of the active ingredient. On application, it was diluted with water and then sprayed or perfused to soil.

PREPARATION EXAMPLE 11

(Emulsifiable concentrate)

Twenty parts of Compound No. 96, 60 parts of xylene and 20 parts of an emulsifier (polyoxyethylene phenylphenol polymer type) were well mixed to obtain an emulsifiable concentrate containing 20% of the active ingredient. On application, it was diluted with water and then sprayed or perfused to soil.

PREPARATION EXAMPLE 12

(Granule)

Ten parts of Compound No. 98, 85 parts of silica powder, 4.95 parts of calcium lignosulfonate and 0.05 part of sodium alkylbenzenesulfonate were well mixed while being powdered. The powder obtained was kneaded with water, granulated and dried to obtain a granule containing 10% of the active ingredient. On application, it was scattered on soil as such or mixed with soil.

PREPARATION EXAMPLE 13

(Liquid)

Fifty parts of Compound No. 100 and 5 parts of a wetting agent (alkylbenzenesulfonate type) were dissolved in 45 parts of water to obtain a liquid containing 50% of the active ingredient. On application, it was diluted with water and then sprayed or perfused to soil.

PREPARATION EXAMPLE 14

(Composite dust)

Five parts of Compound No. 102, 5 parts of pentachloronitrobenzene and 90 parts of clay were well mixed while being powdered to obtain a composite dust containing 10% of the active ingredients.

PREPARATION EXAMPLE 15

(Composite liquid)

Twenty-five parts of Compound No. 95, 25 parts of 5-methyl-3-hydroxy-1,2-oxazole and 5 parts of a wetting agent (alkylbenzenesulfonate type) were dissolved in 45 parts of water to obtain a composite liquid containing 50% of the active ingredient.

PREPARATION EXAMPLE 16

(Composite granule)

Six parts of Compound No. 104, 4 parts of 1,4-dichloro-2,5-dimethoxybenzene, 85 parts of silica powder, 4.95 parts of calcium lignosulfonate and 0.05 part of sodium alkylbenzenesulfonate were well mixed while being powdered. The powder obtained was kneaded with water, granulated and dried to obtain a composite granule containing 10% of the active ingredient.

EXAMPLE 1

Controlling effect against yellows of Japanese radish (*Fusarium oxysporum* f. sp. *raphani*):

Field soil was filled in a plastic pot (diameter, 8 cm) and inoculated by mixing the field soil and infested soil containing cultured *Fusarium oxysporum* f. sp. *raphani* to a depth of 5 cm. On the soil was sowed the seed of radish (variety: Wase-40 nichi) at a rate of 15/pot and covered with soil. Thereafter, the test compound in the form of a liquid preparation was diluted with water and applied at a rate of 15 ml/pot. After three weeks' cultivation in a greenhouse, disease appearance was examined to calculate a percentage of healthy seedlings.

$$\text{Percentage of healthy seedlings (\%)} = \frac{\text{Number of healthy seedlings in each plot}}{\text{Number of germination in untreated and uninoculated plot}} \times 100$$

The results thus obtained are shown in Table 2, and as apparent from the table, the compounds of this invention show an extremely superior controlling effect as compared with the control compounds.

TABLE 2

| Test compound | Dosage of active ingredient (ppm) | Percentage of healthy seedlings (%) | Phytotoxicity |
|---|---|---|---|
| 1 | 250 | 100.0 | — |
| 2 | 250 | 100.0 | — |
| 3 | 250 | 100.0 | — |
| 4 | 250 | 100.0 | — |
| 5 | 250 | 100.0 | — |
| 6 | 250 | 100.0 | — |
| 7 | 250 | 100.0 | — |
| 8 | 250 | 100.0 | — |
| 9 | 250 | 100.0 | — |
| 10 | 250 | 100.0 | — |
| 11 | 250 | 100.0 | — |
| 12 | 250 | 100.0 | — |
| 13 | 250 | 100.0 | — |
| 14 | 250 | 100.0 | — |
| 15 | 250 | 100.0 | — |
| 16 | 250 | 100.0 | — |
| 17 | 250 | 100.0 | — |
| 18 | 250 | 100.0 | — |
| 19 | 250 | 100.0 | — |
| 20 | 250 | 100.0 | — |
| 21 | 250 | 100.0 | — |
| 22 | 250 | 100.0 | — |
| 23 | 250 | 100.0 | — |
| 24 | 250 | 100.0 | — |
| 25 | 250 | 100.0 | — |
| 26 | 250 | 100.0 | — |
| 27 | 250 | 100.0 | — |
| 28 | 250 | 100.0 | — |
| 29 | 250 | 100.0 | — |
| 30 | 250 | 100.0 | — |
| 31 | 250 | 100.0 | — |
| 32 | 250 | 100.0 | — |
| 33 | 250 | 100.0 | — |
| 34 | 250 | 100.0 | — |
| 35 | 250 | 100.0 | — |
| 36 | 250 | 100.0 | — |
| 37 | 250 | 100.0 | — |
| 38 | 250 | 100.0 | — |
| 39 | 250 | 100.0 | — |
| 40 | 250 | 100.0 | — |
| 41 | 250 | 100.0 | — |
| 42 | 250 | 100.0 | — |
| 43 | 250 | 100.0 | — |
| 44 | 250 | 100.0 | — |
| 45 | 250 | 100.0 | — |
| 46 | 250 | 100.0 | — |
| 47 | 250 | 100.0 | — |

TABLE 2-continued

| Test compound | Dosage of active ingredient (ppm) | Percentage of healthy seedlings (%) | Phytotoxicity |
|---|---|---|---|
| 48 | 250 | 100.0 | — |
| 49 | 250 | 100.0 | — |
| 50 | 250 | 100.0 | — |
| 51 | 250 | 100.0 | — |
| 52 | 250 | 100.0 | — |
| 53 | 250 | 100.0 | — |
| 54 | 250 | 100.0 | — |
| 55 | 250 | 100.0 | — |
| 56 | 250 | 100.0 | — |
| 57 | 250 | 100.0 | — |
| 58 | 250 | 100.0 | — |
| 59 | 250 | 100.0 | — |
| 60 | 250 | 100.0 | — |
| 61 | 250 | 100.0 | — |
| 62 | 250 | 100.0 | — |
| 63 | 250 | 100.0 | — |
| 64 | 250 | 100.0 | — |
| 65 | 250 | 100.0 | — |
| 66 | 250 | 100.0 | — |
| 67 | 250 | 100.0 | — |
| 68 | 250 | 100.0 | — |
| 69 | 250 | 100.0 | — |
| 70 | 250 | 100.0 | — |
| 71 | 250 | 100.0 | — |
| 72 | 250 | 100.0 | — |
| 73 | 250 | 100.0 | — |
| 74 | 250 | 100.0 | — |
| 75 | 250 | 100.0 | — |
| 76 | 250 | 100.0 | — |
| 77 | 250 | 100.0 | — |
| 78 | 250 | 100.0 | — |
| 79 | 250 | 100.0 | — |
| 80 | 250 | 100.0 | — |
| 81 | 250 | 100.0 | — |
| 82 | 250 | 100.0 | — |
| 83 | 250 | 100.0 | — |
| 84 | 250 | 100.0 | — |
| 85 | 250 | 100.0 | — |
| 86 | 250 | 100.0 | — |
| 87 | 250 | 100.0 | — |
| 88 | 250 | 100.0 | — |
| 89 | 250 | 100.0 | — |
| 90 | 250 | 100.0 | — |
| 91 | 250 | 100.0 | — |
| 92 | 250 | 100.0 | — |
| 93 | 250 | 100.0 | — |
| 94 | 250 | 100.0 | — |
| 95 | 250 | 100.0 | — |
| 96 | 250 | 100.0 | — |
| 97 | 250 | 100.0 | — |
| 98 | 250 | 100.0 | — |
| 99 | 250 | 100.0 | — |
| 100 | 250 | 100.0 | — |
| 101 | 250 | 100.0 | — |
| 102 | 250 | 100.0 | — |
| 103 | 250 | 100.0 | — |
| 104 | 250 | 100.0 | — |
| Control (a) | 250 | 86.7 | — |
| 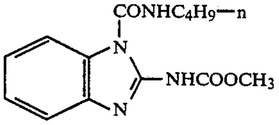 | | | |
| Control (b) | 250 | 77.8 | — |
| 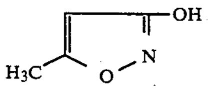 | | | |
| No treatment (inoculated) | — | 6.7 | — |
| No treatment | — | 100.0 | — |

TABLE 2-continued

| Test compound | Dosage of active ingredient (ppm) | Percentage of healthy seedlings (%) | Phyto-toxicity |
|---|---|---|---|
| (non-inoculated) | | | |

EXAMPLE 2

Controlling effect against fusarium wilt of cucumber (*Fusarium oxysporum* f. sp. *cucumerinum*):

Field soil was filled in a plastic cup (diameter, 11 cm) and inoculated by mixing the field soil and infested soil containing cultured *Fusarium oxysporum* f. sp. *cucumerinum* to a depth of 5 cm. On the soil was sowed the seed of cucumber (variety: Shimoshirazuchibai) at a rate of 10/pot and covered with soil. Thereafter, the test compound in the form of an emulsifiable concentrate preparation was diluted with water and applied at a rate of 28 ml/pot. After three weeks' cultivation in a greenhouse, disease appearance was examined to calculate a percentage of healthy seedlings according to the same equation as in Example 1.

The results thus obtained are shown in Table 3, and as apparent from the table, the compounds of this invention show an extremely superior controlling effect as compared with the control compounds.

TABLE 3

| Test compound | Dosage of active ingredient (ppm) | Percentage of healthy seedlings (%) | Phyto-toxicity |
|---|---|---|---|
| 1 | 250 | 100.0 | — |
| 2 | 250 | 100.0 | — |
| 4 | 250 | 100.0 | — |
| 5 | 250 | 100.0 | — |
| 6 | 250 | 100.0 | — |
| 9 | 250 | 100.0 | — |
| 10 | 250 | 100.0 | — |
| 11 | 250 | 100.0 | — |
| 12 | 250 | 100.0 | — |
| 15 | 250 | 100.0 | — |
| 16 | 250 | 100.0 | — |
| 18 | 250 | 100.0 | — |
| 19 | 250 | 100.0 | — |
| 20 | 250 | 100.0 | — |
| 21 | 250 | 100.0 | — |
| 25 | 250 | 100.0 | — |
| 26 | 250 | 100.0 | — |
| 27 | 250 | 100.0 | — |
| 31 | 250 | 100.0 | — |
| 32 | 250 | 100.0 | — |
| 34 | 250 | 100.0 | — |
| 36 | 250 | 100.0 | — |
| 91 | 250 | 100.0 | — |
| 92 | 250 | 100.0 | — |
| 93 | 250 | 100.0 | — |
| 94 | 250 | 100.0 | — |
| 95 | 250 | 100.0 | — |
| 96 | 250 | 100.0 | — |
| 97 | 250 | 100.0 | — |
| 98 | 250 | 100.0 | — |
| 99 | 250 | 100.0 | — |
| 100 | 250 | 100.0 | — |
| 101 | 250 | 100.0 | — |
| 102 | 250 | 100.0 | — |
| 103 | 250 | 100.0 | — |
| 104 | 250 | 100.0 | — |
| Control (a) | 250 | 83.3 | — |

TABLE 3-continued

| Test compound | Dosage of active ingredient (ppm) | Percentage of healthy seedlings (%) | Phyto-toxicity |
|---|---|---|---|
| 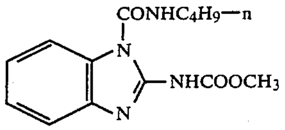 | | | |
| Control (b) | 250 | 76.7 | — |
| 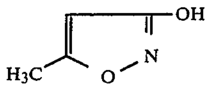 | | | |
| No treatment (inoculated) | — | 6.7 | — |
| No treatment (non-inoculated) | — | 100.0 | — |

EXAMPLE 3

Controlling effect against club-root of vegetables (*Plasmodiophora brassicae*):

Field soil was filled in a plastic vat (0.1 $m^2$) and inoculated by mixing the field soil and infested soil containing cultured *Plasmodiophora brassicae* to a depth of 10 to 15 cm. On the soil was sowed the seed of chinese cabbage (variety: Nozaki No. 2) at a rate of about 50/vat, and covered with soil. Thereafter, the test compound in the form of an emulsifiable concentrate preparation was diluted with water and applied at a rate of 300 ml/vat. After 10 days, the seedlings were thinned to 15/vat, and the aqueous dilute liquor was applied again in the same manner as above. After about one month's cultivation in a greenhouse, disease appearance was examined to calculate a percentage of healthy seedlings:

$$\text{Percentage of healthy seedlings (\%)} = \frac{\text{Number of healthy seedlings in each plot}}{\text{Number of seedlings tested}} \times 100$$

The results thus obtained are shown in Table 4, and as apparent from the table, the compounds of this invention show a superior controlling effect as compared with the control compounds.

TABLE 4

| Test compound | Dosage of active ingredient (ppm) | Percentage of healthy seedlings (%) | Phyto-toxicity |
|---|---|---|---|
| 1 | 500 | 91.1 | — |
| 2 | 500 | 93.4 | — |
| 3 | 500 | 84.5 | — |
| 4 | 500 | 86.7 | — |
| 16 | 500 | 86.7 | — |
| 17 | 500 | 91.1 | — |
| 18 | 500 | 95.6 | — |
| 19 | 500 | 88.1 | — |
| 20 | 500 | 87.5 | — |
| 21 | 500 | 84.5 | — |
| 22 | 500 | 93.4 | — |
| 23 | 500 | 92.7 | — |
| 24 | 500 | 92.7 | — |
| 25 | 500 | 91.1 | — |
| 91 | 500 | 86.7 | — |
| 92 | 500 | 86.7 | — |
| 93 | 500 | 93.4 | — |

TABLE 4-continued

| Test compound | Dosage of active ingredient (ppm) | Percentage of healthy seedlings (%) | Phyto-toxicity |
|---|---|---|---|
| 94 | 500 | 91.1 | — |
| 95 | 500 | 92.7 | — |
| 96 | 500 | 91.3 | — |
| 97 | 500 | 93.4 | — |
| 98 | 500 | 88.1 | — |
| 99 | 500 | 87.5 | — |
| 100 | 500 | 88.1 | — |
| 101 | 500 | 92.7 | — |
| 102 | 500 | 86.7 | — |
| 103 | 500 | 91.1 | — |
| 104 | 500 | 93.4 | — |
| Control (c) | 500 | 71.2 | — |
| 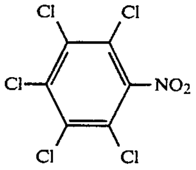 | | | |
| No treatment (inoculated) | — | 2.2 | — |
| No treatment (non-inoculated) | — | 100.0 | — |

EXAMPLE 4

Controlling effect against fusarium wilt of tomato (*Fusarium oxysporum* f. sp. *lycopersici*):

Infested soil containing *Fusarium oxysporum* f. sp. *lycopersici* was filled in a plastic vat (25×33 cm), and young seedlings of tomato (variety: Fukuju No. 2) were transplanted thereto. Thereafter, an aqueous dilute liquor of the test compound was applied to the soil at a rate of 240 ml/vat. After about one month's cultivation in a greenhouse, disease appearance was examined to calculate a percentage of healthy seedlings according to the same equation as in Example 3.

As apparent from Table 5, the compounds of this invention show a superior controlling effect as compared with the control compound.

TABLE 5

| Test compound | Dosage of active ingredient (ppm) | Percentage of healthy seedlings (%) | Phyto-toxicity |
|---|---|---|---|
| 1 | 500 | 100.0 | — |
| 4 | 500 | 100.0 | — |
| 18 | 500 | 100.0 | — |
| Control (a) | 500 | 75.0 | — |
| 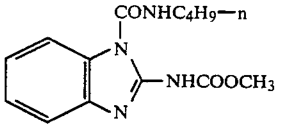 | | | |
| No treatment (inoculated) | — | 0 | — |

What is claimed is:

1. A method for preventing and controlling diseases caused by pathogenic fungi living in soil, which comprises applying an effective amount of phenylphosphinic acid or its salt to the soil where the pathogenic fungi are living.

2. The method according to claim 1, wherein the salt of phenylphosphinic acid is the salt with an inorganic base, the salt with an organic base or the metal salt excluding the alkaline metal salts.

3. The method according to claim 1, wherein the pathogenic fungi is *Furasium oxysporum.*

4. A method for preventing and controlling diseases caused by pathogenic fungi living in soil which comprises applying an effective amount of at least one salt of phenylphosphinic acid with an aliphatic amine to the soil where the pathogenic fungi are living.

5. A method as in claim 4, wherein said aliphatic amine is an alkylamine.

6. A method as in claim 5, wherein said alkylamine is sec-butylamine.

7. A method as in claim 5, wherein said alkylamine is t-butylamine.

8. A method as in claim 5, wherein said alkylamine is isopropylamine.

9. A method as in claim 5, wherein said alkylamine is cyclohexylamine.

10. A method as in claim 4, wherein said aliphatic amine is alcoholamine.

11. A method as in claim 10, wherein said alcoholamine is ethanolamine.

* * * * *